US012617851B2

(12) United States Patent
Andrews et al.

(10) Patent No.: US 12,617,851 B2
(45) Date of Patent: May 5, 2026

(54) TREM2 ANTIBODIES AND USES THEREOF

(71) Applicant: Eli Lilly and Company, Indianapolis, IN (US)

(72) Inventors: Forest Hoyt Andrews, Carmel, IN (US); Ross Edward Fellows, Westfield, IN (US); Ying Tang, San Diego, CA (US); Yaming Wang, Zionsville, IN (US)

(73) Assignee: ELI LILLY AND COMPANY, Indianapolis, IN (US)

( * ) Notice: Subject to any disclaimer, the term of this patent is extended or adjusted under 35 U.S.C. 154(b) by 971 days.

(21) Appl. No.: 17/737,439

(22) Filed: May 5, 2022

(65) Prior Publication Data

US 2022/0281975 A1     Sep. 8, 2022

Related U.S. Application Data

(63) Continuation of application No. PCT/US2020/060663, filed on Nov. 16, 2020.

(60) Provisional application No. 62/939,097, filed on Nov. 22, 2019.

(51) Int. Cl.
| | |
|---|---|
| *C07K 16/00* | (2006.01) |
| *A61K 39/00* | (2006.01) |
| *A61K 39/395* | (2006.01) |
| *A61P 25/28* | (2006.01) |
| *C07K 16/28* | (2006.01) |

(52) U.S. Cl.
CPC .......... *C07K 16/2803* (2013.01); *A61P 25/28* (2018.01); *A61K 2039/505* (2013.01); *C07K 2317/56* (2013.01); *C07K 2317/565* (2013.01); *C07K 2317/76* (2013.01); *C07K 2317/92* (2013.01)

(58) Field of Classification Search
CPC .......... C07K 16/2803; C07K 2317/565; C07K 2317/55; C07K 16/28; C07K 14/70503; C07K 2317/64; C07K 2317/51; C07K 14/705; C07K 2317/515; C07K 2317/54; A61K 2039/505; A61K 47/6849; A61K 38/177; A61K 39/395; A61K 39/39541; A61K 39/001102; A61P 25/28; A61P 25/00; A61P 9/10; A61P 25/16; A61P 25/14; A61P 25/08; G01N 2800/2821; G01N 33/6896; G01N 2333/70503; G01N 33/5058; G01N 33/5055
See application file for complete search history.

(56) References Cited

U.S. PATENT DOCUMENTS

| | | | | |
|---|---|---|---|---|
| 2023/0082623 | A1* | 3/2023 | Papapetropoulos .... | A61P 25/00 424/133.1 |
| 2025/0051429 | A1* | 2/2025 | Freskgard .......... | G01N 33/6896 |

FOREIGN PATENT DOCUMENTS

| | | | | | |
|---|---|---|---|---|---|
| WO | 2016/023019 | A2 | 2/2016 | | |
| WO | 2017/058866 | A1 | 4/2017 | | |
| WO | 2017/062672 | A2 | 4/2017 | | |
| WO | 2018/015573 | A2 | 1/2018 | | |
| WO | 2019/028292 | A1 | 2/2019 | | |
| WO | 2019/055841 | A1 | 3/2019 | | |
| WO | 2019/118513 | A1 | 6/2019 | | |
| WO | WO-2021101823 | A1 * | 5/2021 | .............. | A61P 25/28 |
| WO | WO-2022032293 | A2 * | 2/2022 | ......... | C07K 16/2803 |
| WO | WO-2022120390 | A1 * | 6/2022 | ......... | C07K 16/2803 |
| WO | WO-2025032069 | A1 * | 2/2025 | .............. | A61P 25/28 |
| WO | WO-2025032070 | A1 * | 2/2025 | ......... | G01N 33/6896 |

OTHER PUBLICATIONS

The Factsheet of neurodegenerative diseases retrieved from the Cleveland Clinic website: my.clevelandclinic.org/health/diseases/24976-neurodegenerative-diseases on Jun. 28, 2025.*
The Factsheet of Alzheimer's disease retrieved from the National Institute of Aging website: https://www.nia.nih.gov/health/alzheimers-and-dementia/alzheimers-disease-fact-sheet on Jun. 28, 2025.*
Falkenburger et al., J. Neural. Transm, 2006; 70:261-268.*
Tayebati, Mech. Ageing Dev. 2006. 127: 100-8.*
Sarter, Neurosci. and Biobehav. Rev. 2004. 28: 645-650.*
Henstridge et al. Nat. Rev. Neurosci. 2019; 20: 94-107.*
Swerdlow, Clin. Interv. Ageing 2007; 2:347-359.*
Atwood et al., J. Alzheimer's Disease; 2015; 47:33-47.*
Burgess et al. J of Cell Bio. 1990, 111:2129-2138.*
Pawson et al. 2003, Science 300:445-452.*
Alaoui-Ismaili et al., Cytokine Growth Factor Rev. 2009; 20:501-507.*
Guo et al., PNAS 2004; 101:9205-9210.*
Gratuze Maud et al., :New insights into the role of TREM2 in Alzheimer's Disease Molecular Neurodegeneration, vol. 13, No. 1, Dec. 1, 2018.
Saber Maha et al., "Triggering Receptor Expressed on Myeloid Cells 2 Deficiency Alters Acute Macrophage Distribution and improves Recovery after Traumatic Brain Injury", Journal of Neurotrauma, vol. 34, No. 2, Jan. 15, 2017, pp. 423-435.
Gerlach, et al., TREM2 triggers microglial density and age-related neuronal loss. Glia, 67(3):539-550 (2019).
North, et al., "A New Clustering of Antibody CDR Loop Conformations", Journal of Molecular Biology, 406, 228-256 (2011).
Chothia, et al., "Canonical structures for the hypervariable regions of immunoglobulins", Journal of Molecular Biology, 196, 901-917 (1987).
Al-Lazikani, et al., "Standard conformations for the canonical structures of immunoglobulins", Journal of Molecular Biology, 273, 927-948 (1997).
Mallbris L, et al., J. Clin. Aesthet. Dermatol. 2016; 9: 13-15.
Office Action, CN Application No. 202080079451.2, dated Jul. 7, 2023, 3 pages.
Response to communication under Rules 161(1) and 162 EPC, EP Application No. 20821525.1, Dec. 21, 2022, 5 pages.

(Continued)

*Primary Examiner* — Chang-Yu Wang
(74) *Attorney, Agent, or Firm* — Neelaabh Shankar

(57) ABSTRACT

The present invention relates to TREM2 antibodies, and uses thereof, for treating diseases such as neurodegenerative diseases.

4 Claims, No Drawings

Specification includes a Sequence Listing.

(56)                References Cited

OTHER PUBLICATIONS

Office Action, JP Application No. 2022-529507, dated May 23, 2023, 4 pages.
Written Opinion, Response to Office Action, JP Application No. 2022-529507, dated Aug. 18, 2023, 26 pages.
Decision to Grant a Patent, JP Application No. 2022529507, dated Sep. 27, 2023, 3 pages.
International Search Report, International Application No. PCT/US2020/060663, dated Feb. 25, 2021, 5 pages.
Written Opinion of the International Searching Authority, International Application No. PCT/US2020/060663, dated Feb. 25, 2021, 9 pages.
Examination report No. 1, AU Application No. 2020387380, dated May 6, 2024, 3 pages.
Diepold, et al., "Simultaneous Assessment of Asp Isomerization and Asn Deamidation in Recombinant Antibodies by LC-MS following Incubation at Elevated Temperatures" PLoS One. 7(1):e30295. doi:10.1371/journal.pone.0030295.
EP 20821525.1—Rules 161/162 Communication—Jul. 6, 2022.
Response to Examination Report No. 1, AU Application No. 2020387380, dated Apr. 8, 2025, 10 pages.
Notice of Acceptance, AU Application No. 2020387380, dated Apr. 15, 2025, 3 pages.
Notice of Preliminary Rejection, KR Application No. 10-2022-7016708, dated Feb. 3, 2025, translation, 3 pages.
Written Decision on Registration, KR Application No. 10-2022-7016708, dated Sep. 5, 2025, translation, 3 pages.

* cited by examiner

TREM2 ANTIBODIES AND USES THEREOF

The present invention is in the field of medicine. More particularly, the present invention relates to antibodies that bind to TREM2, compositions comprising such TREM2 antibodies, and methods of using such TREM2 antibodies for the treatment of neurodegenerative diseases such as Alzheimer's disease.

Triggering receptors expressed on myeloid cells 2 (TREM2) is a cell surface transmembrane glycoprotein that is expressed in myeloid cells such as dendritic cells, granulocytes, and tissue-specific macrophages such as osteoclasts, Kuppfer cells, and alveolar macrophages. The TREM2 transmembrane region associates with the adaptor proteins DAP12 and DAP10, and TREM2 signaling through adaptor proteins results in activation of downstream targets such as mTOR and MAPK. TREM2 activation therefore results in activities such as increased proliferation, survival, phagocytosis, phagocytic oxidative burst with production of reactive oxygen species (ROS), as well as pro- and anti-inflammatory cytokine expression. Upon activation of myeloid cells under certain circumstances, membrane-bound TREM2 may be cleaved by proteases, thereby resulting in the release of soluble TREM2.

TREM2 has been implicated in neurodegenerative diseases such as Alzheimer's disease. TREM2 is expressed by microglia in the brain, and increased expression of TREM2 has been observed in Alzheimer's disease patients and in mouse models of tau pathology. Moreover, TREM2 mutations are associated with neurodegenerative diseases and TREM2 knock-out mice have been shown to be protected against age-related inflammatory changes, accumulation of oxidized lipids, and loss of neuronal structures (see, e.g., Gerlach, et al., TREM2 triggers microglial density and age-related neuronal loss. Glia, 67(3):539-550 (2019)). TREM2 deficiency may also be neuroprotective in reducing hippocampal volume loss after traumatic brain injury (see, Saber, et al., Triggering Receptor Expressed on Myeloid Cells 2 Deficiency Alters Acute Macrophage Distribution and Improves Recovery after Traumatic Brain Injury, J. Neurotrauma, 34:423-435 (2017)).

TREM2 antibodies are known in the art. For example, PCT publication number WO 2016/023019 and PCT publication number WO 2019/028292 disclose TREM2 antibodies. Such antibodies may cluster and activate TREM2 in vivo, and/or bind human TREM2 with nanomolar affinity.

Thus, there still exists a need for alternative TREM2 antibodies that 1) bind human TREM2 with desirable high affinity and association and dissociation rates for optimal activity, 2) reduce microglia activation state and/or promote microglia homeostasis without affecting total microglia numbers (e.g., no impact on survival), 3) inhibit TREM2 signaling, 4) achieve in vivo efficacy, 5) demonstrate low immunogenic potential, and/or 6) demonstrate suitable developability characteristics such as stability, solubility, low self-association, and pharmacokinetic characteristics which are acceptable for development and/or use in the treatment of neurodegenerative disorders.

Accordingly, the present invention provides novel TREM2 antibodies that bind human TREM2 with high affinity. Antibodies of the present invention are considered to provide a means to promote microglia homeostasis. Antibodies of the present invention also have at least one of the following properties of reducing microglia activation state, and/or restoring microglia homeostasis, without affecting total microglia numbers (e.g., not impacting on survival), preventing macrophage phagocytosis, inhibiting TREM2 signaling, achieving in vivo efficacy, demonstrating low immunogenic potential, and/or demonstrating suitable developability characteristics for clinical development and/or use in the treatment of neurodegenerative disorders.

Such antibodies may be useful in the treatment of neurodegenerative diseases such as Alzheimer's disease, and may be therapeutically effective at lower doses or less frequent dosing.

In an embodiment, the present invention provides an antibody that binds TREM2, comprising a light chain variable region (LCVR) and a heavy chain variable region (HCVR), wherein the LCVR comprises complementarity determining regions (CDRs) LCDR1, LCDR2, and LCDR3, and the HCVR comprises CDRs HCDR1, HCDR2, and HCDR3, and wherein LCDR1 has an amino acid sequence given by SEQ ID NO: 1, LCDR2 has an amino acid sequence given by SEQ ID NO: 2, LCDR3 has an amino acid sequence given by SEQ ID NO: 3, HCDR1 has an amino acid sequence given by SEQ ID NO: 4, HCDR2 has an amino acid sequence given by SEQ ID NO: 5, and HCDR3 has an amino acid sequence given by SEQ ID NO: 6. In an embodiment, the LCVR has an amino acid sequence given by SEQ ID NO: 7, and the HCVR has an amino acid sequence given by SEQ ID NO: 8. In an embodiment, the antibody comprises a light chain (LC) and a heavy chain (HC), wherein the LC has an amino acid sequence given by SEQ ID NO: 9, and the HC has an amino acid sequence given by SEQ ID NO: 10. In an embodiment, the antibody is a human antibody.

In an embodiment, the present invention provides a DNA molecule comprising a polynucleotide sequence encoding an antibody HC, wherein the HC comprises an amino acid sequence given by SEQ ID NO: 10. In an embodiment, the present invention provides a DNA molecule comprising a polynucleotide sequence encoding an antibody LC, wherein the LC comprises an amino acid sequence given by SEQ ID NO: 9. In an embodiment, the present invention provides a DNA molecule comprising a polynucleotide sequence encoding a HC and LC, wherein the HC comprises an amino acid sequence given by SEQ ID NO: 10, and the LC comprises an amino acid sequence given by SEQ ID NO: 9. In an embodiment, the present invention provides a mammalian cell comprising a DNA molecule comprising a polynucleotide sequence encoding an antibody HC, wherein the HC comprises an amino acid sequence given by SEQ ID NO: 10, and a DNA molecule comprising a polynucleotide sequence encoding an antibody LC, wherein the LC comprises an amino acid sequence given by SEQ ID NO: 9. In an embodiment, the present invention provides a mammalian cell comprising a DNA molecule comprising a polynucleotide sequence encoding a HC and LC, wherein the HC comprises an amino acid sequence given by SEQ ID NO: 10, and the LC comprises an amino acid sequence given by SEQ ID NO: 9.

In an embodiment, the present invention provides a pharmaceutical composition comprising an antibody of the present invention, and one or more pharmaceutically acceptable carriers, diluents, or excipients. In an embodiment, the present invention provides the pharmaceutical composition for use in treating a neurodegenerative disease. In an embodiment, the neurodegenerative disease is Alzheimer's disease, progressive cerebral palsy, multiple sclerosis, ALS, or frontotemporal dementia. In an embodiment, the present invention provides the pharmaceutical composition for use in treating traumatic brain injury.

In an embodiment, the present invention provides a method of treating a patient having a neurodegenerative disease comprising administering to the patient an effective amount of an antibody of the present invention. In an embodiment, the neurodegenerative disease is Alzheimer's disease, progressive cerebral palsy, multiple sclerosis, ALS, or frontotemporal dementia. In an embodiment, the present invention provides a method of treating a patient having traumatic brain injury comprising administering to the patient an effective amount of an antibody of the present invention.

In an embodiment, the present invention also provides an antibody of the present invention for use in therapy. In an embodiment, the present invention provides an antibody of the present invention for use in the treatment of a neurodegenerative disease. In an embodiment, the neurodegenerative disease is Alzheimer's disease, progressive cerebral palsy, multiple sclerosis, ALS, or frontotemporal dementia. In an embodiment, the present invention provides an antibody of the present invention for use in the treatment of traumatic brain injury.

In an embodiment, the present invention provides use of an antibody of the present invention in the manufacture of a medicament for the treatment of a neurodegenerative disease. In an embodiment, the neurodegenerative disease is Alzheimer's disease, progressive cerebral palsy, multiple sclerosis, ALS, or frontotemporal dementia. In an embodiment, the present invention provides use of an antibody of the present invention in the manufacture of a medicament for the treatment of traumatic brain injury.

A "TREM2 antibody" refers to an antibody that binds TREM2 (including TREM2 variants such as the R47H variant) and when administered in vitro or in vivo results in at least one desired activity such as reduced activated microglia.

The term "antibody" as used herein, in regards to the present invention, refers to an engineered, non-naturally occurring polypeptide complex having two HCs and two LCs such that the heavy chains and the light chains are interconnected by disulfide bonds, wherein the antibody is an IgG isotype antibody. Each heavy chain is comprised of an N-terminal HCVR and a heavy chain constant region. Each light chain is comprised of an N-terminal LCVR and a light chain constant region. When expressed in certain biological systems, antibodies are glycosylated in the Fc region. Typically, glycosylation occurs in the Fc region of the antibody at a highly conserved N-glycosylation site. N-glycans typically attach to asparagine. Antibodies may be glycosylated at other positions as well.

The constant region of the heavy chains contains CH1, CH2, and CH3 domains. CH1 comes after the HCVR; the CH1 and HCVR form the heavy chain portion of an antigen-binding (Fab) fragment, which is the part of an antibody that binds antigen(s). CH2 comes after the hinge region and before CH3. CH3 comes after CH2 and is at the carboxy-terminal end of the heavy chain. The constant region of the light chains contains one domain, CL. CL comes after the LCVR; the CL and LCVR form the light chain portion of a Fab.

The HCVR and LCVR regions of an antibody of the present invention can be further subdivided into regions of hyper-variability, termed complementarity determining regions ("CDRs"), interspersed with regions that are more conserved, termed framework regions ("FR"). Each HCVR and LCVR is composed of three CDRs and four FRs, arranged from amino-terminus to carboxy-terminus in the following order: FR1, CDR1, FR2, CDR2, FR3, CDR3, FR4. Herein, the three CDRs of the heavy chain are referred to as "HCDR1, HCDR2, and HCDR3" and the three CDRs of the light chain are referred to as "LCDR1, LCDR2 and LCDR3". The CDRs contain most of the residues which form specific interactions with the antigen. The Kabat CDR definition (Kabat, et al., Ann. NY Acad. Sci. 190:382-93 (1971); Kabat et al., Sequences of Proteins of Immunological Interest, Fifth Edition, U.S. Department of Health and Human Services, NIH Publication No. 91-3242 (1991)) is based upon antibody sequence variability. The Chothia CDR definition (Chothia, et al., "Canonical structures for the hypervariable regions of immunoglobulins", Journal of Molecular Biology, 196, 901-917 (1987); Al-Lazikani, et al., "Standard conformations for the canonical structures of immunoglobulins", Journal of Molecular Biology, 273, 927-948 (1997)) is based on three-dimensional structures of antibodies and topologies of the CDR loops. The Chothia CDR definitions are identical to the Kabat CDR definitions with the exception of HCDR1 and HCDR2. The North CDR definition (North, et al., "A New Clustering of Antibody CDR Loop Conformations", Journal of Molecular Biology, 406, 228-256 (2011)) is based on affinity propagation clustering with a large number of crystal structures. For the purposes of the present invention, assignment of amino acids to CDR domains within the LCVR and HCVR regions of the antibodies of the present invention is based on the well-known Kabat numbering convention.

The antibodies of the present invention are humanized or human antibodies. Preferably, the antibodies are human antibodies. In the context of monoclonal antibodies, the terms "human" (or "fully human") and "humanized" are well-known to those of ordinary skill in the art (Weiner, L. J., J. Immunother. 2006; 29: 1-9; Mallbris L, et al., J. Clin. Aesthet. Dermatol. 2016; 9: 13-15). The antibodies of the present invention may be IgG4PAA antibodies. An IgG4PAA antibody is an IgG4 antibody having a serine to proline substitution and two leucine to alanine substitutions at positions (according to EU numbering) 228, 234, 235, respectively (i.e., S228P, F234A, L235A).

A DNA molecule of the present invention is a DNA molecule that comprises a non-naturally occurring polynucleotide sequence encoding a polypeptide having the amino acid sequence of at least one of the polypeptides in an antibody of the present invention (e.g., heavy chain, light chain, variable heavy chain, or variable light chain).

An isolated DNA encoding a HCVR region can be converted to a full-length heavy chain gene by operably linking the HCVR-encoding DNA to another DNA molecule encoding heavy chain constant regions. The sequences of human, as well as other mammalian, heavy chain constant region genes are known in the art. DNA fragments encompassing these regions can be obtained, e.g., by standard PCR amplification.

An isolated DNA encoding a LCVR region may be converted to a full-length light chain gene by operably linking the LCVR-encoding DNA to another DNA molecule encoding a light chain constant region. The sequences of human, as well as other mammalian, light chain constant region genes are known in the art. DNA fragments encompassing these regions can be obtained by standard PCR amplification. The light chain constant region can be a kappa or lambda constant region. Preferably, for antibodies of the present invention, the light chain constant region is a kappa constant region.

The polynucleotides of the present invention can be expressed in a host cell after the sequences have been operably linked to an expression control sequence. The expression vectors are typically replicable in the host organisms either as episomes or as an integral part of the host chromosomal DNA. Commonly, expression vectors will contain selection markers, e.g., tetracycline, neomycin, and dihydrofolate reductase, to permit detection of those cells transformed with the desired DNA sequences.

The antibodies of the present invention can readily be produced in mammalian cells, non-limiting examples of which includes CHO, NSO, HEK293 or COS cells. The host cells are cultured using techniques well known in the art.

The vectors containing the polynucleotide sequences of interest (e.g., the polynucleotides encoding the polypeptides of the antibody and expression control sequences) can be transferred into the host cell by well-known methods, which vary depending on the type of cellular host.

Various methods of protein purification may be employed to purify proteins, including, but not limited to, antibodies, and such methods are known in the art.

An antibody of the present invention, or a pharmaceutical composition comprising the same, may be administered by parenteral routes, non-limiting examples of which are subcutaneous administration and intravenous administration. An antibody of the present invention may be administered to a patient with pharmaceutically acceptable carriers, diluents, or excipients in single or multiple doses. Pharmaceutical compositions of the present invention can be prepared by methods well known in the art (e.g., Remington: The Science and Practice of Pharmacy, 22nd ed. (2012), Loyd, A., et al., Pharmaceutical Press) and comprise an antibody, as disclosed herein, and one or more pharmaceutically acceptable carriers, diluents, or excipients.

The term "treating" (or "treat" or "treatment") refers to slowing, interrupting, arresting, alleviating, stopping, reducing, or reversing the progression or severity of an existing symptom, disorder, condition, or disease.

"Effective amount" means the amount of a TREM2 antibody of the present invention or pharmaceutical composition comprising such an antibody that will elicit the biological or medical response of or desired therapeutic effect on a tissue, system, animal, mammal, or human that is being sought by the researcher, medical doctor, or other clinician. An effective amount of the antibody may vary according to factors such as the disease state, age, sex, and weight of the individual, and the ability of the antibody to elicit a desired response in the individual. Such benefit includes, and are not limited to, reduced microglia activation and potential to slow brain atrophy or cognition loss. An effective amount can be readily determined by one skilled in the art, by the use of known techniques, and by observing results obtained under analogous circumstances. In determining the effective amount for a patient, a number of factors are considered by the attending diagnostician, including, but not limited to: the patient's size, age, and general health, the specific disease or disorder involved, the degree of, or involvement, or the severity of the disease or disorder, the response of the individual patient, the particular compound administered, the mode of administration, the bioavailability characteristics of the preparation administered, the dose regimen selected, the use of concomitant medication, and other relevant circumstances.

Antibody Engineering

Significant engineering, including antibody germlining, affinity maturation, deimmunization, and drugability optimization, occurred to generate the antibodies of the present invention. Such antibodies are human antibodies that have high affinity for human TREM2, reduced immunogenicity, and acceptable or optimal developability for human clinical studies.

For example, engineering occurred in the heavy chain DSD motif (residues D54, S55, and D56) to reduce isomerization at D54 and/or D56. The serine at position 55 was mutated into either glutamine (S55Q) or histidine (S55H). Both mutations are neutral on antibody affinity. Unexpectedly, the S55Q mutation resulted in a significant reduction of the isomerization from 5.1% to 1%, whereas the S55H mutation increased the isomerization to 63%. Therefore, the S55Q heavy chain mutation reduces isomerization while maintaining binding affinity.

EXAMPLES

Example

Antibody Expression and Purification

TREM2 antibodies of the present invention can be expressed and purified essentially as follows. An appropriate host cell, such as HEK 293 or CHO, can be either transiently or stably transfected with an expression system for secreting antibodies using an optimal predetermined HC:LC vector ratio (such as 1:3 or 1:2) or a single vector system encoding both the HC and the LC. Clarified media, into which the antibody has been secreted, may be purified using any of many commonly-used techniques. For example, the medium may be applied to a MabSelect® column (GE Healthcare), or KappaSelect column (GE Healthcare) for Fab fragment, that has been equilibrated with a compatible buffer, such as phosphate buffered saline (pH 7.4). The column may be washed to remove nonspecific binding components.

The bound antibody may be eluted, for example, by pH gradient (such as 20 mM Tris buffer, pH 7.0 to 10 mM sodium citrate buffer, pH 3.0, or phosphate buffered saline pH 7.4 to 100 mM glycine buffer, pH 3.0). Antibody fractions may be detected, such as by SDS-PAGE, and then may be pooled. Further purification is optional, depending on intended use. The antibody may be concentrated and or sterile filtered using common techniques. Soluble aggregate and multimers may be effectively removed by common techniques, including size exclusion, hydrophobic interaction, ion exchange, multimodal, or hydroxyapatite chromatography. The purity of the antibody after these chromatography steps is between about 95% to about 99%.

The product may be held refrigerated, immediately frozen at −70° C., or may be lyophilized. Amino acid SEQ ID NOs for exemplified human antibodies of the present invention are shown below in Table 1.

TABLE 1

| Amino acid sequences of TREM2 Antibody 1. | | | | | |
|---|---|---|---|---|---|
| LCDR1 | LCDR2 | LCDR3 | HCDR1 | HCDR2 | HCDR3 |
| SEQ ID NO: 1 | SEQ ID NO: 2 | SEQ ID NO: 3 | SEQ ID NO: 4 | SEQ ID NO: 5 | SEQ ID NO: 6 |
| LCVR | | HCVR | | LC | HC |
| SEQ ID NO: 7 | | SEQ ID NO: 8 | | SEQ ID NO: 9 | SEQ ID NO: 10 |

Example

Antibody 1 Binding Kinetics and Affinities to TREM2

Surface plasmon resonance (SPR) at 37° C. is used to determine binding kinetics and affinities of TREM2 antibodies Antibody 1, Reference Antibody A, or Reference Antibody B to antigen. Reference Antibody A comprises a HCVR given by SEQ ID NOs:11, 13, 15, 16, 132, 135, 126, and a LCVR given by SEQ ID NOs: 20, 22, 23, 25, 144, 131, and 129 in PCT publication number WO2019/028292. Reference Antibody B comprises a HCVR and a LCVR as given by SEQ ID NO: 412 and 413, respectively, in PCT publication number WO2016/023019.

The binding kinetics and affinity of TREM2 antibodies to human (SEQ ID NO: 11), mouse (SEQ ID NO: 12), rat (SEQ ID NO: 14), rabbit (SEQ ID NO: 13), or cynomolgus monkey (SEQ ID NO: 15) TREM2 extracellular domains (ECDs) fused to a C-terminal His tag are determined using surface plasmon resonance biosensor such as a BIAcore® T100, BIAcore® T200, or BIAcore® 8K (GE Healthcare, Piscataway, N.).

Samples are dissolved in 1xHBS-EP+running buffer (Teknova), and a protein A coupled CM5 Series S sensor chip (GE Healthcare) is utilized to capture antibody. Binding is evaluated using multiple analytical cycles. Each cycle is performed at 37° C. at a flow rate of 50 μl/min for antibody capture and 30 μl/min for ligand association and dissociation. Each cycle consists of the following: injection of 7 μl of 1 μg/ml antibody with the aim at a capture of 150-250 response units, injection of human, cynomolgus monkey, rabbit, rat, or mouse TREM2-His ECDs (starting at 20nM and using two-fold serial dilutions for each cycle) followed by 200 seconds for association, followed by 800 second dissociation phase, and regeneration using 10 mM glycine hydrochloride, pH 1.5 over a 30 second contact time. Association (i.e., $k_{on}$) and dissociation rates (i.e., $k_{off}$) for each cycle are evaluated using standard double referencing and fit to "1:1 (Langmuir) binding" model in the Biacore 8K evaluation in parallel kinetics batch mode. The affinity ($K_D$) is calculated from the binding kinetics according to the relationship $K_D=K_{off}/K_{on}$. Due to biphasic binding data for Reference Antibody A, a heterogenous ligand 2:1 binding modeling found in the Biacore 8K evaluation was used to calculate the $K_D$. The heterogenous ligand 2:1 reports 2 $k_{on}$ and 2 $k_{off}$ values to calculate the $K_D$ value. N=3 for Antibody 1 and Reference Antibody A, and n=1 for Reference Antibody B.

In experiments performed essentially as described above, the following data were obtained:

TABLE 2

| Binding kinetics and affinity (mean ± standard deviation). | | | |
|---|---|---|---|
| | $k_{on}(M^{-1}s^{-1})$ | $k_{off}(s^{-1})$ | $K_D$ (nM) |
| Human TREM2 | | | |
| Antibody 1 | $3.4 \pm 0.1 \times 10^6$ | $5.8 \pm 0.1 \times 10^{-4}$ | $0.17 \pm 0.01$ |
| Reference Antibody B | $4.9 \pm 0.5 \times 10^5$ | $5.2 \pm 0.5 \times 10^{-3}$ | $9.8 \pm 0.1$ |
| Reference Antibody A* | $7.0 \times 10^6$ $2.1 \times 10^3$ | $0.12$ $5.9 \times 10^{-4}$ | $3.69$ |
| Cyno TREM2 | | | |
| Antibody 1 | $5.0 \times 10^6$ | $3.7 \times 10^{-4}$ | $0.075$ |
| Reference Antibody B | Not tested | Not tested | Not tested |

TABLE 2-continued

| Binding kinetics and affinity (mean ± standard deviation). | | | |
|---|---|---|---|
| | $k_{on}(M^{-1}s^{-1})$ | $k_{off}(s^{-1})$ | $K_D$ (nM) |
| Reference Antibody A* Mouse TREM2 | $1.1 \times 10^7$ $3.1 \times 10^3$ | $0.078$ $6.5 \times 10^{-4}$ | $1.2$ |
| Antibody 1 | $2.5 \pm 0.1 \times 10^7$ | $4.4 \pm 0.5 \times 10^{-2}$ | $1.6 \pm 0.2$ |
| Reference Antibody B | $1.3 \pm 0.1 \times 10^6$ | $2.9 \pm 0.1 \times 10^{-3}$ | $2.1 \pm 0.1$ |
| Reference Antibody A Human TREM2 R47H | ND[#] | ND[#] | ND[#] |
| Antibody 1 Rat TREM2 | $5.0 \times 106$ | $3.7 \times 10 - 4$ | $0.075$ |
| Antibody 1 | ND[#] | ND[#] | ND[#] |
| Reference Antibody B | $2.8 \pm 0.2 \times 10^6$ | $2.1 \pm 0.1 \times 10^{-3}$ | $0.73 \pm 0.03$ |
| Reference Antibody A | ND[#] | ND[#] | ND[#] |

*Binding is biphasic and data fit with heterogeneous ligand binding model resulting in two on rates ($k_{on}$) and two off rates ($k_{off}$).
[#]No binding above background was detected at 200 nM TREM2

These data demonstrate that Antibody 1 bound human TREM2 and cyno TREM2 with high (pM) affinity. Antibody 1 also bound mouse TREM2 with nM affinity and did not bind rat TREM2. Antibody 1 bound human TREM2 with higher affinity compared to Reference Antibody A and Reference Antibody B, and Antibody 1 also bound cynomolgus monkey TREM2 with higher affinity compared to Reference Antibody A. No binding was detected with rabbit TREM2 for any antibody tested.

Similar experiments were performed at 25° C. and the following data were obtained. Antibody 1 bound human, mouse, and cynomolgus monkey TREM, and human R47H TREM mutant, with binding affinities of 150 pM, 3.9 nM, 43 pM, and 290 pM, respectively. The R47H mutant has been associated with developing Alzheimer's disease. These data demonstrate that Antibody 1 is able to bind R47H TREM.

Example

Antibody 1 Binding to TREM2-Expressing Cells

To investigate whether Antibody 1 binds to TREM2-expressing cells, a binding experiment is performed. BW5147.G.1.4 cell line is transduced to express human TREM2 and its adapter DNAZ adapter protein 12 (DAP12). To assess binding, 500,000 cells are incubated in the presence of Antibody 1 with a 3-fold 12-point titration starting at 30 μg/ml for 30 minutes at 37° C. Antibody binding is detected using goat anti-human IgG Alexa Fluor 647 (Jackson Labs). Mean fluorescence intensity (MFI) is measured using an Accuri C6 Plus flow cytometer (BD Biosciences).

Following procedures essentially as described above, Antibody 1 bound to TREM2 expressing BW5147.G.1.4 cells with an $EC_{50}$ of 0.08 μg/ml. These data demonstrated that Antibody 1 binds to cell membrane bound TREM2.

Example

Inhibition of TREM2 Signaling

To investigate the impact of TREM2 antibody-mediated NFAT activation in the presence of ligand, phosphatidylserine (PS, Avanti lipids) is used as a TREM2 ligand. A 96-well plate containing 1.5 mM PS per well is dried at room temperature for three hours. TREM2 NFAT luciferase BW5147.G.14 reporter cells (400,000 cells per well) are plated onto PS-coated plates in the presence of isotype control antibody or Antibody 1, with a 5-fold, 8-point titration starting at 30 µg/ml. After an 18-hour incubation at 37° C., luminescence is detected using the Pierce Firefly Luciferase Flash Assay kit (Thermo Fisher) and Envision 2105 plate reader (Perkin Elmer).

In an experiment performed essentially as described above, Antibody 1 inhibited PS-mediated NFAT activation in a concentration dependent manner with an $IC_{50}$ of 0.40 µg/ml. Control antibody did not inhibit PS-mediated NFAT activation. These data demonstrate that Antibody 1 can inhibit ligand triggered TREM2 signaling.

Example

Inhibition of TREM2 Activation in Macrophages

To investigate the impact of Antibody 1 on TREM2 activation in macrophages, macrophages are cultured on top of PDAPP brain tissue section (which contain physiological endogenous ligands of TREM2) in the presence or absence of Antibody 1 or isotype control antibody.

Bone marrow derived macrophage are generated by culturing bone marrow cells for 5 days in the presence of 50 ng/ml CSF-1 (PEPROTECH). To induce TREM2 activation, 400,000 macrophages are plated on brain tissue section from PDAPP amyloid precursor transgenic mice for three days in the presence of 3 µg/ml or 12 µg/ml control antibody or Antibody 1. Levels of osteopontin, a direct product of TREM2 activation, is measured in the supernatant using an ELISA kit (R&D Systems).

Following procedures essentially as described above, the following data were obtained.

TABLE 3

Macrophage osteopontin levels (pg/ml) in the presence or absence of Antibody 1.

|  | Macrophage | Macrophage + PDAPP brain | PDAPP brain |
|---|---|---|---|
| No antibody (control) | 38652 ± 2033 | 127475 ± 4863 | 7 ± 3 |

| | Macrophage + PDAPP brain | |
|---|---|---|
|  | 3 µg/ml antibody | 12 µg/ml antibody |
| Control Antibody | 125141 ± 30602 | 109078 ± 37666 |
| Antibody 1 | 57803 ± 5706 | 38834 ± 16348 |

These data demonstrate that 3 µg/ml and 12 µg/ml of Antibody 1 inhibited the production of osteopontin. These results indicate that Antibody 1 inhibits TREM2 activation in response to physiological ligands.

Example

Impact of Antibody 1 on Microglia Activation State During Tau-Mediated Neurodegeneration In Vivo To evaluate the impact of Antibody 1 on microglia activation state during tau-mediated neurodegeneration in vivo, Antibody 1 is administered to seven-month old female rTg4510 P301L tau transgenic mice on days zero, with a 3-fold, 6 point titration starting at 300 mg per gram of body weight. On day seven, mice are sacrificed and brain tissue is harvested for RNA analyses. Clec7a, a TREM2 dependent gene is measured in the hippocampus using a Taqman qPCR assay, and relative expression is normalized to the house keeping gene Hprt.

Following procedures essentially as described above, the following data were obtained.

TABLE 4

Relative Clec7a expression after Antibody 1 treatment (+/−SEM)

| Antibody 1 (mg/kg) | 300 | 100 | 30 | 10 | 3 | 1 |
|---|---|---|---|---|---|---|
| Relative Clec7a expression | 9.9 ± 1.0 | 13.4 ± 4.0 | 13.8 ± 1.0 | 19. ± 2.0 | 16 ± 2.0 | 18 ± 1.0 |

These data demonstrate an antibody concentration dependent reduction of Clec7a level in hippocampus following treatment with Antibody 1 and indicate that Antibody 1 inhibits TREM2 in vivo. Levels of soluble TREM2 were also determined and a dose-dependent increase of soluble TREM2 in the CSF was observed.

Example

Major Histocompatibility Complex-Associated Peptide Proteomics

To investigate the immunogenic potential of Antibody 1, major histocompatibility complex-associated peptide proteomics (MAPPs) assay is performed. Primary human dendritic cells from ten normal human donors are prepared from buffy coats by isolation of CD14 positive cells with anti-CD14 beads and a magnetic separator. The CD14 positive cells were plated at 5'6 cells per well and differentiated into immature dendritic cells by incubation with 20 ng/mL IL-4 and 40 ng/mL GM-CSF in complete RPMI media containing 10% fetal bovine serum for 3 days at 37° C. and 5% $CO_2$. Four days later (day four), the media is exchanged and fresh media containing 3 µM of antibody is added to the cells. On day five, 5 µg/ml of LPS is added to transform the cells into mature dendritic cells. On day six, the cells are lysed in 1 mL of RIPA buffer with protease inhibitors and lysate is frozen at −80° C.

Samples are prepared for MHC-II isolation by thawing the frozen lysate and homogenizing for 5-10 seconds. The homogenized lysates are clarified by centrifugation. Immunoprecipitation of MHC-II complexes are performed using biotinylated anti-MHC-II antibody coupled to streptavidin beads. The bound complex is eluted with 5% acetic acid, 0.1% TFA. The MHC-II peptides are separated from co-eluting receptor proteins by passing the eluate over a pre-washed 10k MWCO filter. The isolated MHC-II peptides are analyzed by nano LC/MS using a Thermo QE-HFX mass spectrometer. Peptide identifications are generated by a proteomics pipeline using search algorithms with no enzyme and a bovine/human database with test antibody sequences appended to determine the percentage of donors displaying MHC-II peptides from complementarity determining regions of the antibody tested.

Following procedures essentially as described above, Antibody 1 demonstrated a low risk of immunogenicity as shown by 0% donors that displayed non-germline clusters in heavy chain CDR3.

SEQUENCES
Antibody 1 LCDR1

(SEQ ID NO: 1)

RASQAIRDDLG

Antibody 1 LCDR2

(SEQ ID NO: 2)

YAASSLQS

Antibody 1 LCDR3

(SEQ ID NO: 3)

LQNYNYPHT

Antibody 1 HCDR1

(SEQ ID NO: 4)

GFSFNTYWIG

Antibody 1 HCDR2

(SEQ ID NO: 5)

IIYPGDQDIRYSPSFQG

Antibody 1 HCDR3

(SEQ ID NO: 6)

ARYGRYIYGYGGYHGMDV

Antibody 1 LCVR (SEQ ID NO: 7)

DIQMTQSPSSLSASVGDRVTITCRASQAIRDDLGWYQQKPGKAPKLLIYAA

SSLQSGVPSRFSGSGSGTDFTLTISSLQPEDFATYYCLQNYNYPHTFGQGT

KLEIK

Antibody 1 HCVR (SEQ ID NO: 8)

EVQLVQSGAEVKKPGESLKISCKGSGFSFNTYWIGWVRQMPGKGLEWMGII

YPGDQDIRYSPSFQGQVTISADKSISTAYLQWSSLKASDTAMYYCARYGRY

IYGYGGYHGMDVWGQGTTVTVSS

Antibody 1 LC (SEQ ID NO: 9)

DIQMTQSPSSLSASVGDRVTITCRASQAIRDDLGWYQQKPGKAPKLLIYAA

SSLQSGVPSRFSGSGSGTDFTLTISSLQPEDFATYYCLQNYNYPHTFGQGT

KLEIKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLSSP

VTKSFNRGEC

Antibody 1 HC (SEQ ID NO: 10)

EVQLVQSGAEVKKPGESLKISCKGSGFSFNTYWIGWVRQMPGKGLEWMGIT

YPGDQDIRYSPSFQGQVTISADKSISTAYLQWSSLKASDTAMYYCARYGRY

IYGYGGYHGMDVWGQGTTVTVSSASTKGPSVFPLAPCSRSTSESTAALGCL

-continued

VKDYFPEPVTVSWNSGALTSGVHTFPAVLQSSGLYSLSSVVTVPSSSLGTK

TYTCNVDHKPSNTKVDKRVESKYGPPCPPCPAPEAAGGPSVFLFPPKPKDT

LMISRTPEVTCVVVDVSQEDPEVQFNWYVDGVEVHNAKTKPREEQFNSTYR

VVSVLTVLHQDWLNGKEYKCKVSNKGLPSSIEKTISKAKGQPREPQVYTLP

PSQEEMTKNQVSLTCLVKGFYPSDIAVEWESNGQPENNYKTTPPVLDSDGS

FFLYSRLTVDKSRWQEGNVFSCSVMHEALHNHYTQKSLSLSLG

Human ECD TREM2-His (SEQ ID NO: 11)

HNTTVFQGVAGQSLQVSCPYDSMKHWGRRKAWCRQLGEKGPCQRVVSTHNL

WLLSFLRRWNGSTAITDDTLGGTLTITLRNLQPHDAGLYQCQSLHGSEADT

LRKVLVEVLADPLDHRDAGDLWFPGESESFEDAHVEHSISRSLLEGEIPFP

PTSHHHHHH

Mouse ECD TREM2-His (SEQ ID NO: 12)

LNTTVLQGMAGQSLRVSCTYDALKHWGRRKAWCRQLGEEGPCQRVVSTHGV

WLLAFLKKRNGSTVIADDTLAGTVTITLKNLQAGDAGLYQCQSLRGREAEV

LQKVLVEVLEDPLDDQDAGDLWVPEESSSFEGAQVEHSTSRNQETSFPPTS

HHHHHH

Rabbit ECD TREM2-HIS (SEQ ID NO: 13)

NTTVFQGVAGQSLRVSCPYDSATHWGRRKAWCRQLGEEGPCERVVSTHSWW

LLSFLKRRNGSTAITDDALGGTLTVTLRDLQAQDAGVYQCQSLQGREASTL

QKILVEVLTEPLEHEHAGDFWVPEESGSFEDPPVERSSSRSPSEGEPSFPP

ASGGGGQHHHHHH

Rat ECD TREM2-His (SEQ ID NO: 14)

NTTVLQGVAGQSLRVSCTYDALRHWGRRKAWCRQLAEEGPCQRVVSTHGVW

LLAFLRKQNGSTVITDDTLAGTVTITLRNLQAGDAGLYQCQSLRGREAEVL

QKVVVEVLEDPLDDQDAGDLWVPEESESFEGAQVEHSTSRSQSGGGGQHHH

HHH

Cyno ECD TREM2-His (SEQ ID NO: 15)

HNTTVFQGVEGQSLQVSCPYDSMKHWGRRKAWCRQLGEKGPCQRVVSTHNL

WLLSFLRRRNGSTAITDDTLGGTLTITLRNLQPHDAGFYQCQSLHGSEADT

LRKVLVEVLADPLDHRDAGDLWVPGESESFEDAHVEHSISRPSQGSHLPSC

LSKEGGGGQHEIHHHH

We claim:

1. An antibody that binds Triggering receptors expressed on myeloid cells 2 (TREM2), comprising a light chain variable region (LCVR) and a heavy chain variable region (HCVR), wherein the LCVR comprises complementarity determining regions (CDRs) LCDR1, LCDR2, and LCDR3, and the HCVR comprises CDRs HCDR1, HCDR2, and HCDR3, and wherein the LCDR1 has the amino acid sequence of SEQ ID NO: 1, the LCDR2 has the amino acid sequence of SEQ ID NO: 2, the LCDR3 has the amino acid sequence of SEQ ID NO: 3, the HCDR1 has the amino acid sequence of SEQ ID NO: 4, the HCDR2 has the amino acid sequence of SEQ ID NO: 5, and the HCDR3 has the amino acid sequence of SEQ ID NO: 6.

2. The antibody of claim 1, wherein the LCVR has the amino acid sequence of SEQ ID NO: 7, and the HCVR has the amino acid sequence of SEQ ID NO: 8.

3. The antibody of claim 1, wherein the antibody comprises a LC and a HC, and wherein the LC has the amino acid sequence of SEQ ID NO: 9, and the HC has the amino acid sequence of SEQ ID NO: 10.

4. A pharmaceutical composition comprising the antibody of claim 1, and one or more pharmaceutically acceptable carriers, diluents, or excipients.

* * * * *

SEQUENCE LISTING

<160> NUMBER OF SEQ ID NOS: 15

<210> SEQ ID NO 1
<211> LENGTH: 11
<212> TYPE: PRT
<213> ORGANISM: Artificial Sequence
<220> FEATURE:
<223> OTHER INFORMATION: Synthetic Construct

<400> SEQUENCE: 1

Arg Ala Ser Gln Ala Ile Arg Asp Asp Leu Gly
1               5                   10

```
<210> SEQ ID NO 2
<211> LENGTH: 8
<212> TYPE: PRT
<213> ORGANISM: Artificial Sequence
<220> FEATURE:
<223> OTHER INFORMATION: Synthetic Construct

<400> SEQUENCE: 2

Tyr Ala Ala Ser Ser Leu Gln Ser
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic Construct

<400> SEQUENCE: 3

Leu Gln Asn Tyr Asn Tyr Pro His Thr
1               5

<210> SEQ ID NO 4
<211> LENGTH: 10
<212> TYPE: PRT
<213> ORGANISM: Artificial Sequence
<220> FEATURE:
<223> OTHER INFORMATION: Synthetic Construct

<400> SEQUENCE: 4

Gly Phe Ser Phe Asn Thr Tyr Trp Ile Gly
1               5                   10

<210> SEQ ID NO 5
<211> LENGTH: 17
<212> TYPE: PRT
<213> ORGANISM: Artificial Sequence
<220> FEATURE:
<223> OTHER INFORMATION: Synthetic Construct

<400> SEQUENCE: 5

Ile Ile Tyr Pro Gly Asp Gln Asp Ile Arg Tyr Ser Pro Ser Phe Gln
1               5                   10                  15

Gly

<210> SEQ ID NO 6
<211> LENGTH: 18
<212> TYPE: PRT
<213> ORGANISM: Artificial Sequence
<220> FEATURE:
<223> OTHER INFORMATION: Synthetic Construct

<400> SEQUENCE: 6

Ala Arg Tyr Gly Arg Tyr Ile Tyr Gly Tyr Gly Gly Tyr His Gly Met
1               5                   10                  15

Asp Val

<210> SEQ ID NO 7
<211> LENGTH: 107
<212> TYPE: PRT
<213> ORGANISM: Artificial Sequence
<220> FEATURE:
<223> OTHER INFORMATION: Synthetic Construct

<400> SEQUENCE: 7
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ala Ile Arg Asp Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asn Tyr Asn Tyr Pro His
                85                  90                  95

Thr Phe Gly Gln Gly Thr Lys Leu Glu Ile Lys
            100                 105

<210> SEQ ID NO 8
<211> LENGTH: 125
<212> TYPE: PRT
<213> ORGANISM: Artificial Sequence
<220> FEATURE:
<223> OTHER INFORMATION: Synthetic Construct

<400> SEQUENCE: 8

Glu Val Gln Leu Val Gln Ser Gly Ala Glu Val Lys Lys Pro Gly Glu
1               5                   10                  15

Ser Leu Lys Ile Ser Cys Lys Gly Ser Gly Phe Ser Phe Asn Thr Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Gln Asp Ile Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Tyr Gly Arg Tyr Ile Tyr Gly Tyr Gly Gly Tyr His Gly Met
            100                 105                 110

Asp Val Trp Gly Gln Gly Thr Thr Val Thr Val Ser Ser
        115                 120                 125

<210> SEQ ID NO 9
<211> LENGTH: 214
<212> TYPE: PRT
<213> ORGANISM: Artificial Sequence
<220> FEATURE:
<223> OTHER INFORMATION: Synthetic Construct

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ala Ile Arg Asp Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
```

-continued

```
65                    70                    75                    80

Glu Asp Phe Ala Thr Tyr Tyr Cys Leu Gln Asn Tyr Asn Tyr Pro His
                85                    90                    95

Thr Phe Gly Gln Gly Thr Lys Leu Glu Ile Lys Arg Thr Val Ala Ala
                100                   105                   110

Pro Ser Val Phe Ile Phe Pro Pro Ser Asp Glu Gln Leu Lys Ser Gly
                115                   120                   125

Thr Ala Ser Val Val Cys Leu Leu Asn Asn Phe Tyr Pro Arg Glu Ala
                130                   135                   140

Lys Val Gln Trp Lys Val Asp Asn Ala Leu Gln Ser Gly Asn Ser Gln
145                   150                   155                   160

Glu Ser Val Thr Glu Gln Asp Ser Lys Asp Ser Thr Tyr Ser Leu Ser
                165                   170                   175

Ser Thr Leu Thr Leu Ser Lys Ala Asp Tyr Glu Lys His Lys Val Tyr
                180                   185                   190

Ala Cys Glu Val Thr His Gln Gly Leu Ser Ser Pro Val Thr Lys Ser
                195                   200                   205

Phe Asn Arg Gly Glu Cys
    210

<210> SEQ ID NO 10
<211> LENGTH: 451
<212> TYPE: PRT
<213> ORGANISM: Artificial Sequence
<220> FEATURE:
<223> OTHER INFORMATION: Synthetic Construct

<400> SEQUENCE: 10

Glu Val Gln Leu Val Gln Ser Gly Ala Glu Val Lys Lys Pro Gly Glu
1                   5                     10                    15

Ser Leu Lys Ile Ser Cys Lys Gly Ser Gly Phe Ser Phe Asn Thr Tyr
                20                    25                    30

Trp Ile Gly Trp Val Arg Gln Met Pro Gly Lys Gly Leu Glu Trp Met
                35                    40                    45

Gly Ile Ile Tyr Pro Gly Asp Gln Asp Ile Arg Tyr Ser Pro Ser Phe
                50                    55                    60

Gln Gly Gln Val Thr Ile Ser Ala Asp Lys Ser Ile Ser Thr Ala Tyr
65                    70                    75                    80

Leu Gln Trp Ser Ser Leu Lys Ala Ser Asp Thr Ala Met Tyr Tyr Cys
                85                    90                    95

Ala Arg Tyr Gly Arg Tyr Ile Tyr Gly Tyr Gly Gly Tyr His Gly Met
                100                   105                   110

Asp Val Trp Gly Gln Gly Thr Thr Val Thr Val Ser Ser Ala Ser Thr
                115                   120                   125

Lys Gly Pro Ser Val Phe Pro Leu Ala Pro Cys Ser Arg Ser Thr Ser
                130                   135                   140

Glu Ser Thr Ala Ala Leu Gly Cys Leu Val Lys Asp Tyr Phe Pro Glu
145                   150                   155                   160

Pro Val Thr Val Ser Trp Asn Ser Gly Ala Leu Thr Ser Gly Val His
                165                   170                   175

Thr Phe Pro Ala Val Leu Gln Ser Ser Gly Leu Tyr Ser Leu Ser Ser
                180                   185                   190

Val Val Thr Val Pro Ser Ser Ser Leu Gly Thr Lys Thr Tyr Thr Cys
                195                   200                   205

Asn Val Asp His Lys Pro Ser Asn Thr Lys Val Asp Lys Arg Val Glu
```

-continued

```
        210                 215                 220

Ser Lys Tyr Gly Pro Pro Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                    245                 250                 255

Met Ile Ser Arg Thr Pro Glu Val Thr Cys Val Val Val Asp Val Ser
                260                 265                 270

Gln Glu Asp Pro Glu Val Gln Phe Asn Trp Tyr Val Asp Gly Val Glu
            275                 280                 285

Val His Asn Ala Lys Thr Lys Pro Arg Glu Glu Gln Phe Asn Ser Thr
        290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
                340                 345                 350

Val Tyr Thr Leu Pro Pro Ser Gln Glu Glu Met Thr Lys Asn Gln Val
            355                 360                 365

Ser Leu Thr Cys Leu Val Lys Gly Phe Tyr Pro Ser Asp Ile Ala Val
        370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
                420                 425                 430

Met His Glu Ala Leu His Asn His Tyr Thr Gln Lys Ser Leu Ser Leu
            435                 440                 445

Ser Leu Gly
    450

<210> SEQ ID NO 11
<211> LENGTH: 162
<212> TYPE: PRT
<213> ORGANISM: Artificial Sequence
<220> FEATURE:
<223> OTHER INFORMATION: Synthetic Construct

<400> SEQUENCE: 11

His Asn Thr Thr Val Phe Gln Gly Val Ala Gly Gln Ser Leu Gln Val
1               5                   10                  15

Ser Cys Pro Tyr Asp Ser Met Lys His Trp Gly Arg Arg Lys Ala Trp
                20                  25                  30

Cys Arg Gln Leu Gly Glu Lys Gly Pro Cys Gln Arg Val Val Ser Thr
            35                  40                  45

His Asn Leu Trp Leu Leu Ser Phe Leu Arg Arg Trp Asn Gly Ser Thr
        50                  55                  60

Ala Ile Thr Asp Asp Thr Leu Gly Gly Thr Leu Thr Ile Thr Leu Arg
65                  70                  75                  80

Asn Leu Gln Pro His Asp Ala Gly Leu Tyr Gln Cys Gln Ser Leu His
                85                  90                  95

Gly Ser Glu Ala Asp Thr Leu Arg Lys Val Leu Val Glu Val Leu Ala
            100                 105                 110

Asp Pro Leu Asp His Arg Asp Ala Gly Asp Leu Trp Phe Pro Gly Glu
```

-continued

```
            115                 120                 125

Ser Glu Ser Phe Glu Asp Ala His Val Glu His Ser Ile Ser Arg Ser
    130                 135                 140

Leu Leu Glu Gly Glu Ile Pro Phe Pro Pro Thr Ser His His His His
145                 150                 155                 160

His His

<210> SEQ ID NO 12
<211> LENGTH: 159
<212> TYPE: PRT
<213> ORGANISM: Artificial Sequence
<220> FEATURE:
<223> OTHER INFORMATION: Synthetic Construct

<400> SEQUENCE: 12

Leu Asn Thr Thr Val Leu Gln Gly Met Ala Gly Gln Ser Leu Arg Val
1               5                   10                  15

Ser Cys Thr Tyr Asp Ala Leu Lys His Trp Gly Arg Arg Lys Ala Trp
                20                  25                  30

Cys Arg Gln Leu Gly Glu Glu Gly Pro Cys Gln Arg Val Val Ser Thr
            35                  40                  45

His Gly Val Trp Leu Leu Ala Phe Leu Lys Lys Arg Asn Gly Ser Thr
        50                  55                  60

Val Ile Ala Asp Asp Thr Leu Ala Gly Thr Val Thr Ile Thr Leu Lys
65                  70                  75                  80

Asn Leu Gln Ala Gly Asp Ala Gly Leu Tyr Gln Cys Gln Ser Leu Arg
                    85                  90                  95

Gly Arg Glu Ala Glu Val Leu Gln Lys Val Leu Val Glu Val Leu Glu
            100                 105                 110

Asp Pro Leu Asp Asp Gln Asp Ala Gly Asp Leu Trp Val Pro Glu Glu
            115                 120                 125

Ser Ser Ser Phe Glu Gly Ala Gln Val Glu His Ser Thr Ser Arg Asn
    130                 135                 140

Gln Glu Thr Ser Phe Pro Pro Thr Ser His His His His His His
145                 150                 155

<210> SEQ ID NO 13
<211> LENGTH: 166
<212> TYPE: PRT
<213> ORGANISM: Artificial Sequence
<220> FEATURE:
<223> OTHER INFORMATION: Synthetic Construct

<400> SEQUENCE: 13

Asn Thr Thr Val Phe Gln Gly Val Ala Gly Gln Ser Leu Arg Val Ser
1               5                   10                  15

Cys Pro Tyr Asp Ser Ala Thr His Trp Gly Arg Arg Lys Ala Trp Cys
                20                  25                  30

Arg Gln Leu Gly Glu Glu Gly Pro Cys Glu Arg Val Val Ser Thr His
            35                  40                  45

Ser Trp Trp Leu Leu Ser Phe Leu Lys Arg Arg Asn Gly Ser Thr Ala
        50                  55                  60

Ile Thr Asp Asp Ala Leu Gly Gly Thr Leu Thr Val Thr Leu Arg Asp
65                  70                  75                  80

Leu Gln Ala Gln Asp Ala Gly Val Tyr Gln Cys Gln Ser Leu Gln Gly
                    85                  90                  95

Arg Glu Ala Ser Thr Leu Gln Lys Ile Leu Val Glu Val Leu Thr Glu
```

-continued

```
                100                 105                 110

Pro Leu Glu His Glu His Ala Gly Asp Phe Trp Val Pro Glu Glu Ser
            115                 120                 125

Gly Ser Phe Glu Asp Pro Pro Val Glu Arg Ser Ser Ser Arg Ser Pro
        130                 135                 140

Ser Glu Gly Glu Pro Ser Phe Pro Pro Ala Ser Gly Gly Gly Gly Gln
145                 150                 155                 160

His His His His His His
                165

<210> SEQ ID NO 14
<211> LENGTH: 156
<212> TYPE: PRT
<213> ORGANISM: Artificial Sequence
<220> FEATURE:
<223> OTHER INFORMATION: Synthetic Construct

<400> SEQUENCE: 14

Asn Thr Thr Val Leu Gln Gly Val Ala Gly Gln Ser Leu Arg Val Ser
1               5                   10                  15

Cys Thr Tyr Asp Ala Leu Arg His Trp Gly Arg Arg Lys Ala Trp Cys
            20                  25                  30

Arg Gln Leu Ala Glu Glu Gly Pro Cys Gln Arg Val Val Ser Thr His
        35                  40                  45

Gly Val Trp Leu Leu Ala Phe Leu Arg Lys Gln Asn Gly Ser Thr Val
        50                  55                  60

Ile Thr Asp Asp Thr Leu Ala Gly Thr Val Thr Ile Thr Leu Arg Asn
65                  70                  75                  80

Leu Gln Ala Gly Asp Ala Gly Leu Tyr Gln Cys Gln Ser Leu Arg Gly
                85                  90                  95

Arg Glu Ala Glu Val Leu Gln Lys Val Val Val Glu Val Leu Glu Asp
            100                 105                 110

Pro Leu Asp Asp Gln Asp Ala Gly Asp Leu Trp Val Pro Glu Glu Ser
        115                 120                 125

Glu Ser Phe Glu Gly Ala Gln Val Glu His Ser Thr Ser Arg Ser Gln
        130                 135                 140

Ser Gly Gly Gly Gly Gln His His His His His His
145                 150                 155

<210> SEQ ID NO 15
<211> LENGTH: 168
<212> TYPE: PRT
<213> ORGANISM: Artificial Sequence
<220> FEATURE:
<223> OTHER INFORMATION: Synthetic Construct

<400> SEQUENCE: 15

His Asn Thr Thr Val Phe Gln Gly Val Glu Gly Gln Ser Leu Gln Val
1               5                   10                  15

Ser Cys Pro Tyr Asp Ser Met Lys His Trp Gly Arg Arg Lys Ala Trp
            20                  25                  30

Cys Arg Gln Leu Gly Glu Lys Gly Pro Cys Gln Arg Val Val Ser Thr
        35                  40                  45

His Asn Leu Trp Leu Leu Ser Phe Leu Arg Arg Arg Asn Gly Ser Thr
    50                  55                  60

Ala Ile Thr Asp Asp Thr Leu Gly Gly Thr Leu Thr Ile Thr Leu Arg
65                  70                  75                  80
```

-continued

```
Asn Leu Gln Pro His Asp Ala Gly Phe Tyr Gln Cys Gln Ser Leu His
                85                  90                  95

Gly Ser Glu Ala Asp Thr Leu Arg Lys Val Leu Val Glu Val Leu Ala
            100             105             110

Asp Pro Leu Asp His Arg Asp Ala Gly Asp Leu Trp Val Pro Gly Glu
        115             120             125

Ser Glu Ser Phe Glu Asp Ala His Val Glu His Ser Ile Ser Arg Pro
        130             135             140

Ser Gln Gly Ser His Leu Pro Ser Cys Leu Ser Lys Glu Gly Gly Gly
145             150             155             160

Gly Gln His His His His His His
                165
```